US00PP27576P3

(12) United States Plant Patent
Lyrene

(10) Patent No.: US PP27,576 P3
(45) Date of Patent: Jan. 24, 2017

(54) BLUEBERRY PLANT NAMED 'FL03-228'

(50) Latin Name: ***Vaccinium corymbosum* L.**
Varietal Denomination: FL03-228

(71) Applicant: Florida Foundation Seed Producers, Inc., Marianna, FL (US)

(72) Inventor: Paul M. Lyrene, Micanopy, FL (US)

(73) Assignee: Florida Foundation Seed Producers, Inc., Marianna, FL (US)

( * ) Notice: Subject to any disclaimer, the term of this patent is extended or adjusted under 35 U.S.C. 154(b) by 136 days.

(21) Appl. No.: 14/544,722

(22) Filed: Feb. 9, 2015

(65) Prior Publication Data

US 2015/0237775 P1 Aug. 20, 2015

(30) Foreign Application Priority Data

Feb. 14, 2014 (QZ) ..... PBR 2014/0349

(51) Int. Cl.
*A01H 5/08* (2006.01)

(52) U.S. Cl.
USPC ..... Plt./157

(58) Field of Classification Search
USPC ..... Plt./157
See application file for complete search history.

(56) References Cited

U.S. PATENT DOCUMENTS

PP11,807 P2 3/2001 Lyrene
PP19,341 P2 10/2008 Lyrene

OTHER PUBLICATIONS

"Interspecific Crosses and Backcrosses between Diploid Vaccinium darrowii and Tetraploid Southern Highbush Blueberry," Chavez and Lyrene, J. Amer. Soc. Hort. Sci. 134(2):273-280. 2009.*
U.S. Appl. No. 14/544,781, filed Feb. 12, 2015, Lyrene et al.

* cited by examiner

*Primary Examiner* — Anne Grunberg
(74) *Attorney, Agent, or Firm* — Dentons US LLP

(57) ABSTRACT

'FL03-228' is a new and distinct southern highbush blueberry (*Vaccinium corymbosum* L.) variety distinguished by a very low chilling requirement, tolerance to fungal leaf diseases that cause defoliation, and fruit that are large, firm, and sweet, with a small, dry picking scar.

6 Drawing Sheets

Latin name of the genus and species of the plant claimed: *Vaccinium corymbosum* L.

Variety denomination: 'FL03-228'.

CROSS REFERENCE TO RELATED APPLICATIONS

This application claims the benefit of European Community Plant Breeders Rights Appl. No. 2014/0349, filed Feb. 14, 2014, herein incorporated by reference in its entirety.

BACKGROUND OF THE INVENTION

The present invention relates to a new and distinct hybrid variety of southern highbush blueberry (*Vaccinium corymbosum* L.) named 'FL03-228'. 'FL03-228' is a blueberry clone distinguished by its low chilling requirement, vigorous, upright-spreading bush, and sweet, firm berries that ripen in a concentrated period from late-March through April when grown under evergreen conditions. Several hundred plants of 'FL03-228' have been propagated by softwood stem cuttings in Gainesville, Fla. USA and near Lalla Mimouna, Morocco, and the resulting plants have all been phenotypically indistinguishable from the original plant. Contrast is made to 'Jewel' (U.S. Plant Pat. No. 11,807), an important variety worldwide southern highbush blueberry production. The claimed plant is important because it is has larger and firmer fruit than 'Jewel' during a similar harvest period, and it is more resistant to fungal leaf diseases than 'Jewel'.

'FL03-228' originated as a seedling from a cross between the proprietary parent 'FL00-30' (unpatented) as the female (seed) parent and 'Farthing' (U.S. Plant Pat. No. 19,341) as the male (pollen) parent. This cross was made as part of a breeding program in a greenhouse at Gainesville, Fla. USA, in February 2000. The seedling was planted in a high-density field nursery in May 2001, and the first fruit were evaluated in April 2002. After the second year of fruiting in the field, in the spring of 2003, 'FL03-228' was asexually propagated by softwood stem cuttings in Citra, Fla., and an experimental 15-plant test plot was established as part of a variety test at Windsor, Fla. USA, in January 2004. 'FL03-228' was not repropagated for further testing in Florida, but based on the growth, yield, and fruit quality of this plot, 'FL03-228' was repropagated by softwood stem cuttings and experimental test plots ranging from 50 to several hundred plants were established near Lalla Mimouna, Morocco. These plots have been observed during flowering and ripening each year, and no mutations or off-type plants have been observed.

'FL03-228' differs from the proprietary parent 'FL00-30' (unpatented) in that 'FL03-228' has a greater tendency toward evergreeness and earlier maturing fruit. 'FL03-228' differs from the parent 'Farthing' (U.S. Plant Pat. No. 19,341) in that 'FL03-228' has a greater tendency toward evergreeness, is earlier maturing, and has better blue color. 'FL03-228' differs from the commercial variety 'Jewel' (U.S. Plant Pat. No. 11,807), an important variety planted worldwide for early production, in that 'FL03-228' has high yields of large, firm fruit during an earlier, concentrated harvest period. 'FL03-228' also is less susceptible to fungal leaf diseases that cause defoliation than 'Jewel'.

SUMMARY OF THE INVENTION

Blueberry variety 'FL03-228' exhibits outstanding and distinguishing characteristics when grown under evergreen horticultural practices in Morocco, including: (1) a vigorous, upright-spreading bush; (2) early ripening (50% ripe berries in Morocco around March 30); and (3) large, sweet, low-acid, firm berries with a small, dry picking scar.

BRIEF DESCRIPTION OF THE DRAWINGS

The accompanying photographs show typical bush, flower, and fruit characteristics for 'FL03-228'. Colors shown are as true as can be reasonably reproduced by photographic procedures and may differ from those cited in the detailed description, which accurately describes the colors of 'FL03-228'.

DETAILED BOTANICAL DESCRIPTION

Figure 1:
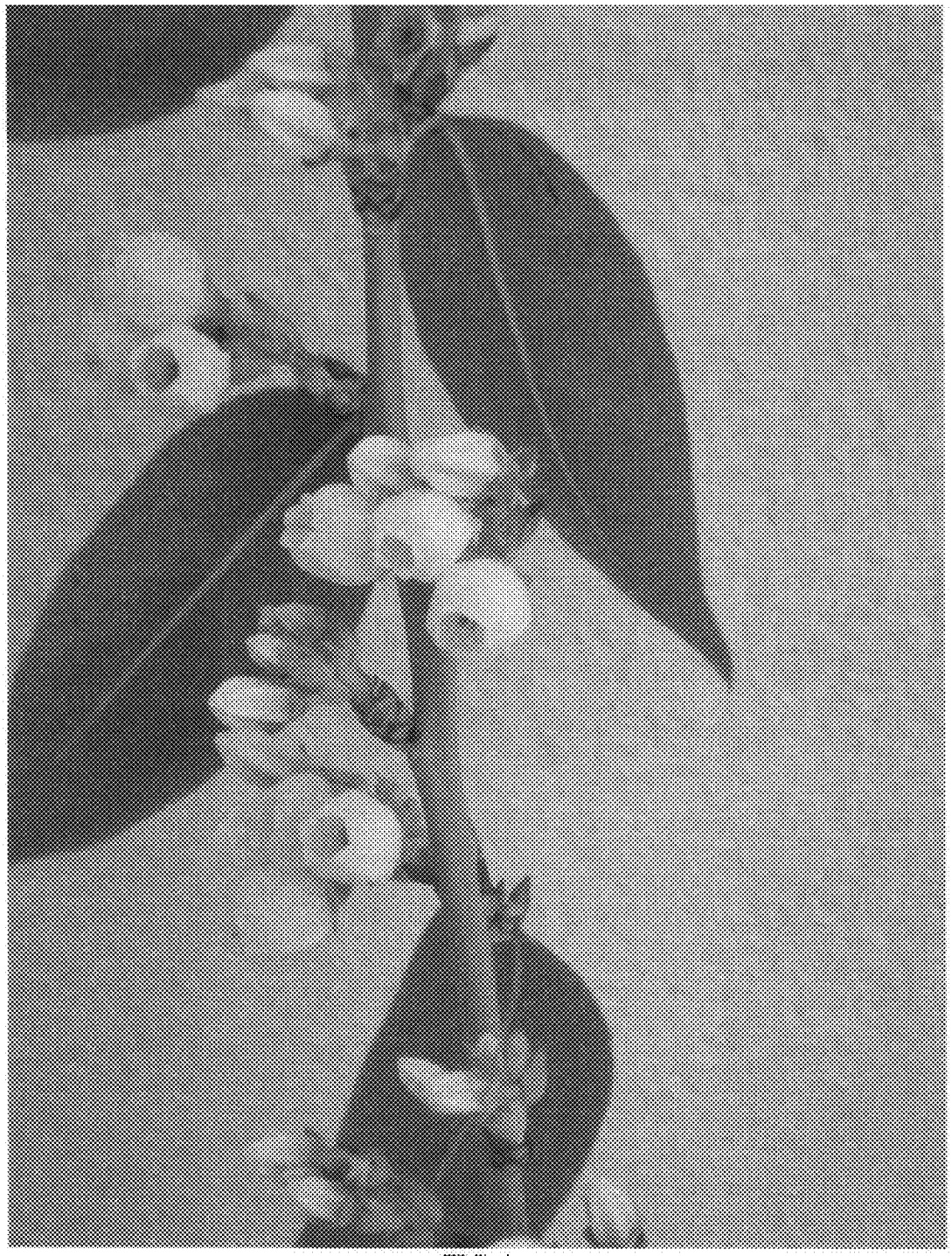
FIG. 1—Shows several clusters of opening 'FL03-228' flowers during the early stages of flowering in March.
Figure 2:
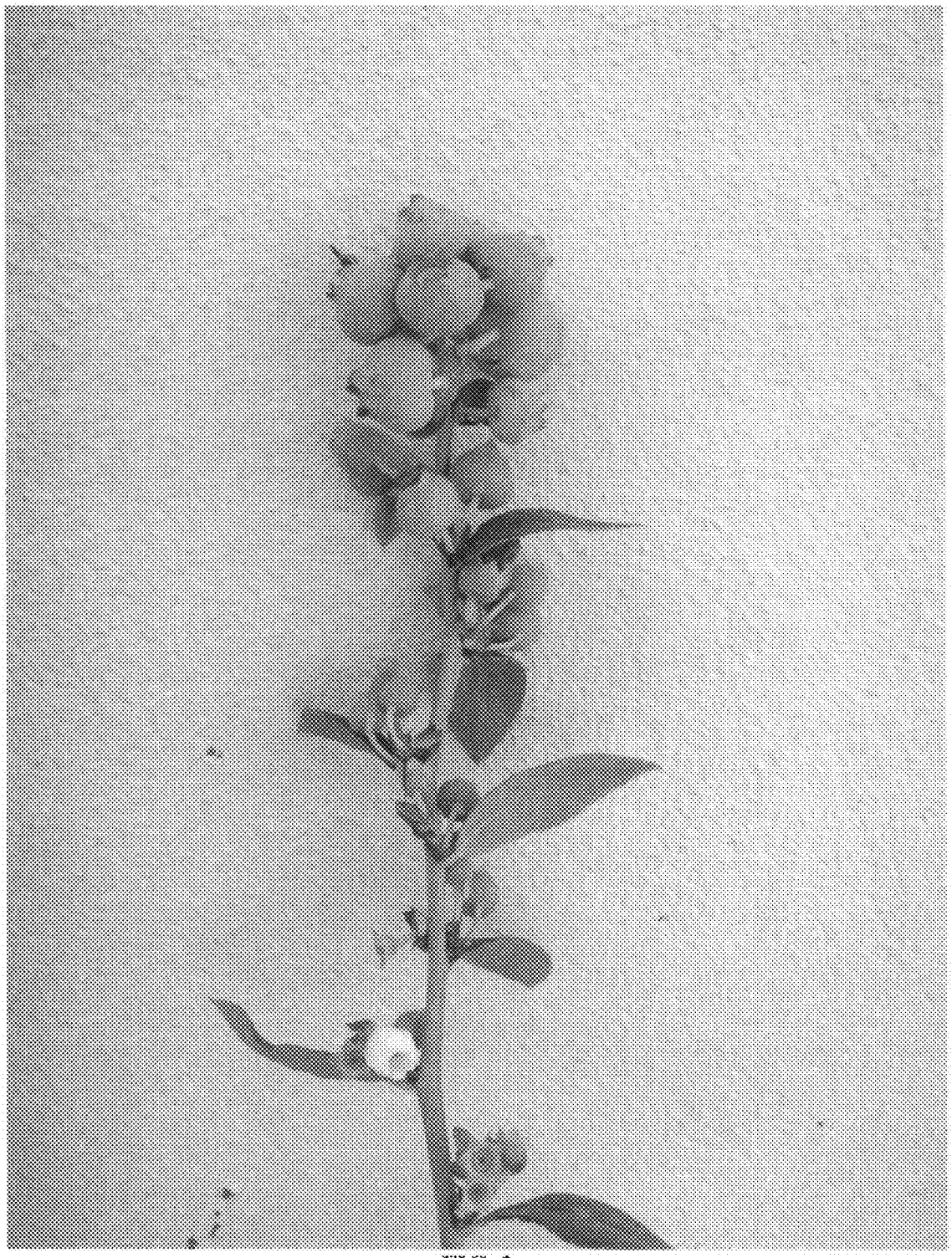
FIG. 2—Shows several clusters of 'FL03-228' berries during the fruit ripening season.
Figure 3:
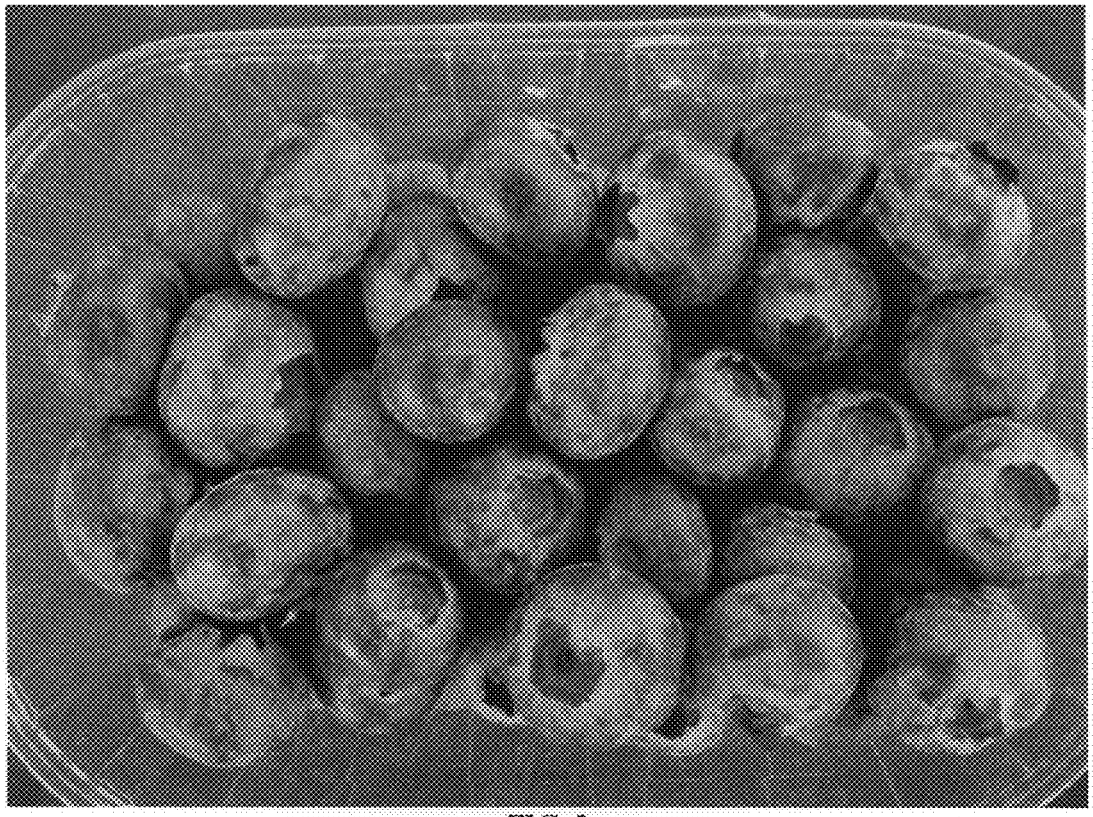
FIG. 3—Shows a close-up of harvested 'FL03-228' berries.
Figure 4:
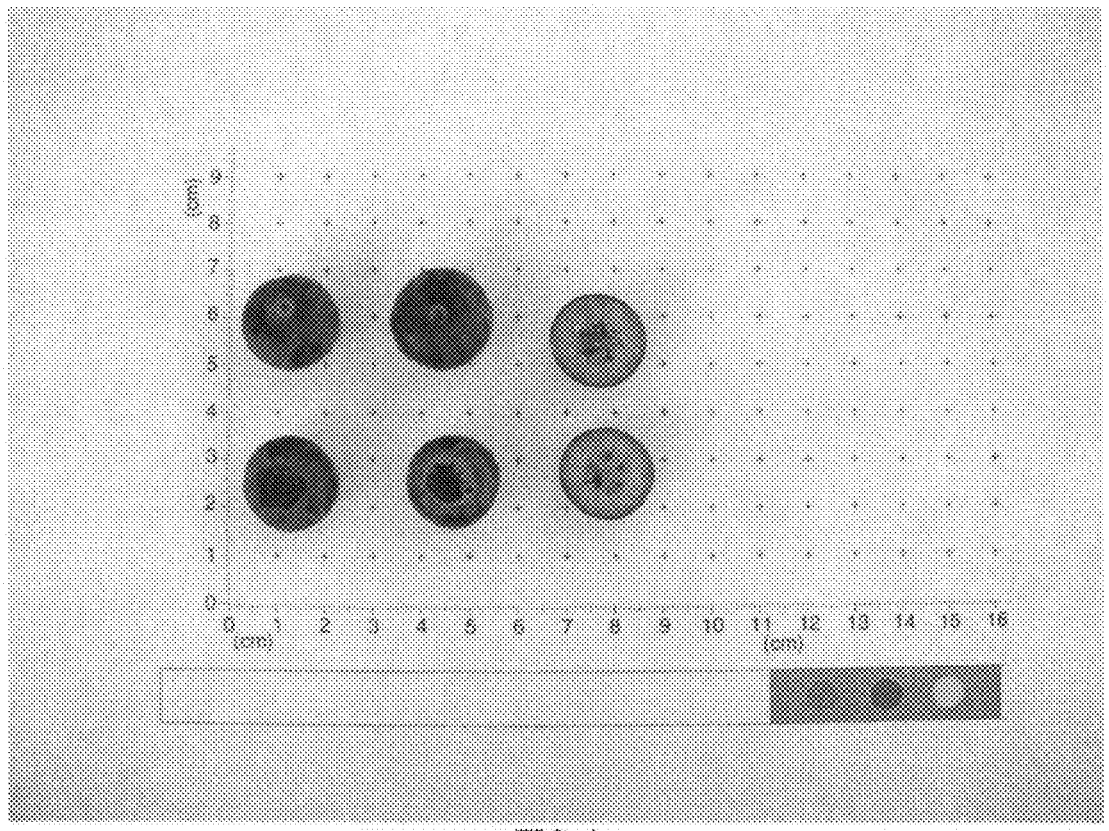
FIG. 4—Shows a close-up of mature 'FL03-228' fruit with a scale bar.
Figure 5:
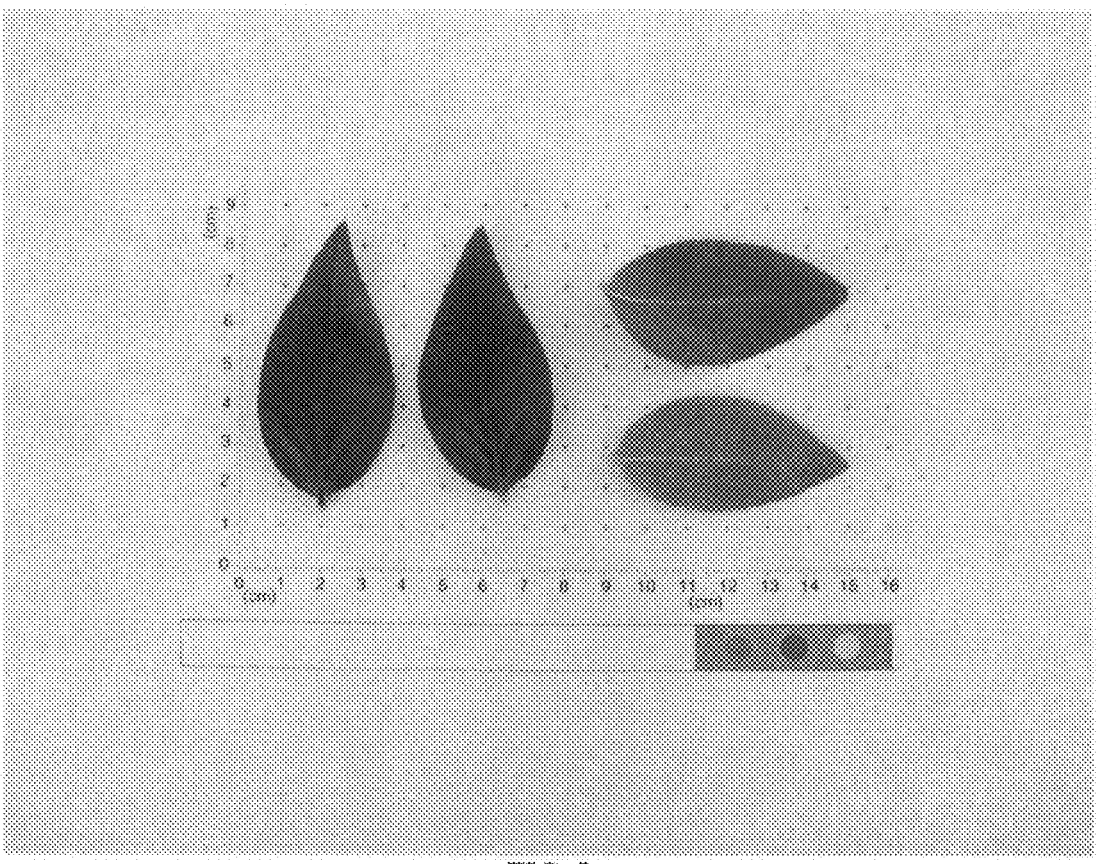
FIG. 5—Shows a close-up of 'FL03-228' leaves with a scale bar.
Figure 6:
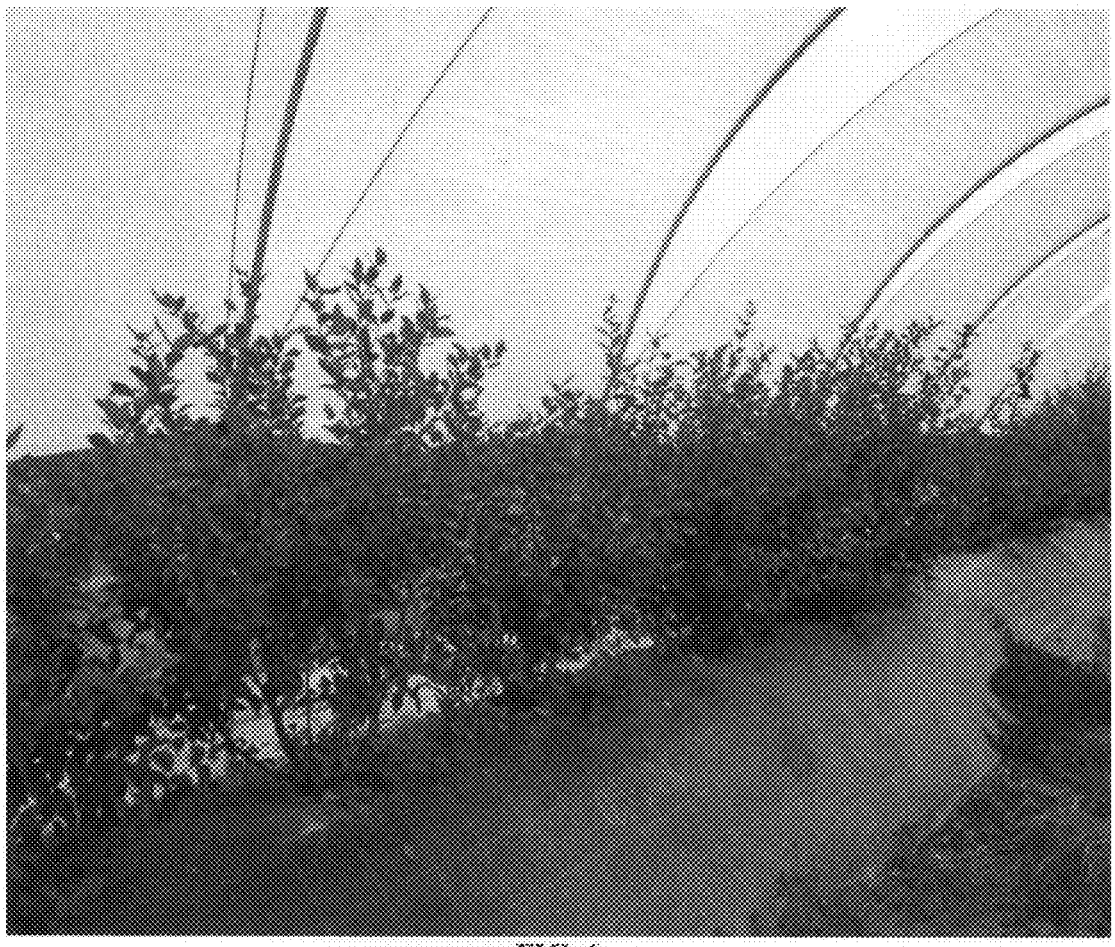
FIG. 6—Shows several two-year-old 'FL03-228' plants during the vegetative growth period near Lalla Mimouna, Morocco.

The following detailed description sets forth the distinctive characteristics of 'FL03-228'. The data that define these characteristics were collected from asexual reproductions carried out in Lalla Mimouna, Morocco. The plant history was taken on a plot of 50 seven-year-old plants growing in a commercial field near Lalla Mimouna, Morocco. Certain characteristics may vary with plant age. 'FL03-228' has not been observed under all possible environmental conditions, and the measurements given may vary when grown in different environments. Where means are given, the sample size was 20. Color descriptions are based on The Royal Horticultural Society (R.H.S.) Colour Chart by The Royal Horticultural Society, London, Fifth Edition, 2007. When the RHS color designations differ from the accompanying photographs, the RHS color designations are accurate.

PHENOTYPIC DESCRIPTION OF *VACCINIUM CORYMBOSUM* L. ('FL03-228')

Plant:

*Plant vigor*.—Medium.

*Growth habit*.—Upright-spreading.

*Flower bud density (number) along flowering twigs in March*.—High.

*Twigginess*.—Medium.

*Tendency toward evergreenness*.—High.

*Productivity*.—In trials in Morocco, 'FL03-228' was very productive, with higher marketable yields than 'Jewel' (U.S. Plant Pat. No. 11,807).

*Chilling requirement*.—'FL03-228' has performed best under evergreen production conditions where chilling is not calculated. 'FL03-228' flowered and leafed well in areas receiving an average of 300 chill hours (0 to 7° C.) when trialed in Florida, USA as a deciduous plant.

*Cold hardiness*.—'FL03-228' has not been grown in temperate climates with extremely cold winter temperatures. Plants have survived winter freezes of −6° C. with minimal damage.

*Ease of propagation*.—'FL03-228' has only been propagated from softwood stem cuttings, where the rooting percentage is typically comparable to other varieties.

Trunk and branches:

*Suckering tendency*.—Medium. Three-year-old plants typically have 5 to 7 major canes arising from a crown 30 cm in diameter.

*Surface texture (of strong, 6-month-old shoots observed in march)*.—Smooth.

*Surface texture (of 3-year-old and older wood)*.—Rough.

*Color of new twigs observed in the field*.—Yellow-green N144D.

*Color of 3-year-old, rough-textured canes*.—Brown N200B.

*Internode length (strong, upright shoots measured in march)*.—Mean of 23.4 mm.

Leaves:

*Length (including petiole, from tip of petiole to end of blade)*.—Mean of 6.6 cm.

*Width (at widest point)*.—Mean of 3.0 cm.

*Shape*.—Elliptic, with a rounded base and acute tip.

*Margin*.—Entire.

*Color*.—Upper surface: Green N137A. Lower surface: Yellow-green 148B.

*Pubescence*.—Upper surface of leaves: Absent. Lower surface of leaves: Absent. Margins: Absent.

*Relative time of leafing versus flowering*.—When grown as an evergreen plant, leafing is delayed relative to flowering.

Flowers:

*Arrangement*.—Flowers are arranged alternately along a short, leafless, deciduous branch.

*Fragrance*.—None.

*Shape*.—Urceolate.

*Flowering period*.—The bloom period when observed under evergreen production in Morocco is from January to February.

*Cluster (tight, medium, loose)*.—Medium.

*Number of flowers per cluster*.—Mean of 4.7.

*Pedicel*.—Length at time of anthesis: Mean of 7.2 mm. Color at time of anthesis: Yellow-green 150C with Greyed-red 179C on sun-exposed side.

*Peduncle*.—Length at time of anthesis: Highly variable, mean of 12.6 mm. Color at time of anthesis: Yellow-green 154D with Red 53B on sun-exposed side.

*Calyx*.—Surface texture: Smooth and waxy. Diameter: Mean of 6.3 mm. Color: Green 139C to Yellow-green 144D on tips of calyx lobes.

*Corolla*.—Diameter: Mean of 8.3 mm. Length (from pedicel attachment point to corolla tip excluding the pedicel): Mean of 11.3 mm. Aperture diameter: Mean of 4.5 mm. Texture: Smooth. Color: White 155D.

Reproductive organs:

*Style*.—Length (top of ovary to stigma tip): Mean of 10.4 mm. Color: Yellow-green 150C. Location of tip of stigma relative to lip of the corolla — Stigma tip is approximately 1 mm below the corolla lip.

*Anthers*.—Color: Greyed-orange 163B. Pollen — Abundance of shed: High. Color: Yellow-white 158A.

*Self-fruitfulness*.—Low to medium. Planting in field configurations that promote cross fertilization with other southern highbush varieties is recommended for all southern highbush blueberry plants.

Fruit: Mean date of 50% harvest near Lalla Mimouna, Morocco is March 30.

*Diameter of calyx aperture on mature berry*.—Mean of 6.0 mm.

*Size and shape of calyx lobes on mature berry*.—Small to medium lobes, erect. Medium calyx basin.

*Pedicel length on ripe berry*.—Mean of 12.4 mm.

*Detachment force for ripe berries* (*easy, medium, hard*).—Medium.

*Number of berries per cluster*.—Mean of 4.7.

Berry:

*Cluster* (*tight, medium, loose*).—Medium to tight.

*Weight* (*on well-pruned plants*).—Mean of 2.9 g.

*Height*.—Mean of 14.1 mm.

*Width*.—Mean of 18.9 mm.

*Shape*.—Oblate, with small fruit tending toward round.

*Surface color of mature berries ripe on the plant*.—Violet-blue 98D.

*Surface color of ripe berry after polishing*.—Greyed-purple N186A.

*Immature berry color, with bloom*.—Greyed-green 194C.

*Immature berry color without bloom*.—Yellow-green 144B.

*Surface wax*.—Medium. The surface wax on 'FL03-228' has only moderate persistence.

*Pedicel scar*.—Small and dry. Mean of 2.2 mm.

*Firmness*.—Very firm.

*Flavor*.—Sweet, good sugar:acid balance.

*Texture*.—Firm, juicy, small seeds, and no stone cells present.

Seeds:

*Color of dried seeds*.—Greyed-orange N167A.

*Length of well-developed dried seed*.—Mean of 2.3 mm.

*Width of well-developed dried seed*.—Mean of 1.2 mm.

Use: 'FL03-228' produces southern highbush blueberries suitable for fresh markets. 'FL03-228' has performed best in trials when grown under an evergreen management system.

Resistance to diseases, insects, and mites: 'FL03-228' has grown vigorously and shows excellent bush survival when grown under protected cultivation in an evergreen management system. 'FL03-228' appears to have excellent resistance to the fungal species that cause fall leaf spots. Resistance of 'FL03-228' to fungal leaf spots, is greater than that of 'Jewel' (U.S. Plant Pat. No. 11,807).

What is claimed is:

1. A new and distinct southern highbush blueberry plant named 'FL03-228', as illustrated and described herein.

* * * * *